US011840491B2

(12) United States Patent
Dagle et al.

(10) Patent No.: US 11,840,491 B2
(45) Date of Patent: Dec. 12, 2023

(54) SYSTEMS AND METHODS FOR PREPARING BUTENES

(71) Applicant: Battelle Memorial Institute, Richland, WA (US)

(72) Inventors: Vanessa Dagle, Richland, WA (US); Robert A. Dagle, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 0 days.

(21) Appl. No.: 17/846,476

(22) Filed: Jun. 22, 2022

(65) Prior Publication Data
US 2022/0411348 A1 Dec. 29, 2022

Related U.S. Application Data

(60) Provisional application No. 63/213,275, filed on Jun. 22, 2021.

(51) Int. Cl.
*C07C 1/22* (2006.01)
*B01J 23/72* (2006.01)
(Continued)

(52) U.S. Cl.
CPC ............... *C07C 1/22* (2013.01); *B01J 8/1881* (2013.01); *B01J 8/24* (2013.01); *B01J 21/066* (2013.01);
(Continued)

(58) Field of Classification Search
CPC ..... C07C 1/2076; C07C 1/22; C07C 2521/06; C07C 2521/08; C07C 2523/72;
(Continued)

(56) References Cited

U.S. PATENT DOCUMENTS 3,481,999 A 12/1969 Reich
10,647,622 B1 5/2020 Dagle et al.
(Continued)

FOREIGN PATENT DOCUMENTS

CA 2572510 6/2007
WO WO 2014/008355 1/2014
(Continued)

OTHER PUBLICATIONS

Dagle et al. ("Integrated process for the catalytic conversion of biomass-derived syngas into transportation fuels." Green Chem., 2016, 18, 1880) (Year: 2016).*

*Primary Examiner* — In Suk C Bullock
*Assistant Examiner* — Jason Y Chong
(74) *Attorney, Agent, or Firm* — Wells St. John P.S.

(57) ABSTRACT

Systems for preparing butenes are provided. The systems can include a reactor inlet coupled to both a reactor and at least one reactant reservoir; at least one of the reactant reservoirs containing one or both of an aldehyde and/or ethanol; a catalyst within the reactor, the catalyst comprising a metal component and an acidic support material; and a reactor outlet operationally configured to convey a butene-rich reaction product to a product reservoir. Methods for preparing butenes are also provided. The methods can include exposing one or both of ethanol and/or an aldehyde to a catalyst comprising a metal component and an acidic support to form a butene-rich product that comprises one or both of 1-butene and/or 2-butene.

6 Claims, 3 Drawing Sheets

(51) Int. Cl.
 *B01J 8/24* (2006.01)
 *B01J 8/18* (2006.01)
 *B01J 21/08* (2006.01)
 *B01J 21/06* (2006.01)

(52) U.S. Cl.
 CPC ............... *B01J 21/08* (2013.01); *B01J 23/72* (2013.01); *C07C 2521/06* (2013.01); *C07C 2521/08* (2013.01); *C07C 2523/72* (2013.01)

(58) Field of Classification Search
 CPC ............ C07C 2529/03; C07C 2529/072; B01J 8/005; B01J 8/008; B01J 8/1881; B01J 8/24; B01J 21/066; B01J 21/08; B01J 21/12; B01J 23/72; B01J 29/0333; B01J 29/072; B01J 4/02
 See application file for complete search history.

(56) References Cited

U.S. PATENT DOCUMENTS

| | | |
|---|---|---|
| 11,046,623 B1 | 6/2021 | Dagle et al. |
| 2002/0193638 A1* | 12/2002 | Warren ............... C07D 261/08 568/354 |
| 2020/0048170 A1* | 2/2020 | Li ..................... B01J 37/0201 |
| 2020/0165176 A1* | 5/2020 | Dagle .................... C07C 11/08 |

FOREIGN PATENT DOCUMENTS

| | | |
|---|---|---|
| WO | WO PCT/US22/34480 | 9/2022 |
| WO | WO PCT/US22/34480 | 11/2022 |

\* cited by examiner

SYSTEMS AND METHODS FOR PREPARING BUTENES

CROSS REFERENCE TO RELATED APPLICATION

This application claims priority to and the benefit of U.S. Provisional Patent Application Ser. No. 63/213,275 filed Jun. 22, 2021, entitled "Process and Catalysts for Making Linear Butenes-Rich Olefins from Aldehyde, Ethanol, or Mixtures Thereof", the entirety of which is incorporated by reference herein.

STATEMENT AS TO RIGHTS TO DISCLOSURES MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

TECHNICAL FIELD

The present disclosure provides systems and methods for preparing olefins. In particular embodiments, the present disclosure provides systems and methods for preparing olefin-rich products including 1-butene and/or 2-butene from ethanol and/or aldehydes.

BACKGROUND

Petroleum depletion and environmental concerns have led to renewed interest in using biomass as a carbon source for the production of biofuels. Ethanol and ethanol-derived aldehyde conversion to biofuels represent an appealing bioenergy technology. Accordingly, ethanol and ethanol-derived aldehydes are commercially produced from renewable biomass or waste sources. Additionally, an ethanol "blend wall" coupled with advancements in production efficiency and feedstock diversification may potentially lead to excess ethanol having competitive pricing for the production of a wide range of fuels and/or commodity chemicals. Moreover, with the lightening of feedstocks to steam crackers, due to the increasing use of shale gas instead of naphtha as feed, there may be a shortage of $C_3$ and $C_4$ olefins as industrial starting materials.

SUMMARY

Systems for preparing butenes are provided. The systems can include a reactor inlet coupled to both a reactor and at least one reactant reservoir; at least one of the reactant reservoirs containing one or both of an aldehyde and/or ethanol; a catalyst within the reactor, the catalyst comprising a metal component and an acidic support material; and a reactor outlet operationally configured to convey a butene-rich reaction product to a product reservoir.

Methods for preparing butenes are also provided. The methods can include exposing one or both of ethanol and/or an aldehyde to a catalyst comprising a metal component and an acidic support to form a butene-rich product that comprises one or both of 1-butene and/or 2-butene.

DRAWINGS

Embodiments of the disclosure are described below with reference to the following accompanying drawings.

Figure 3:
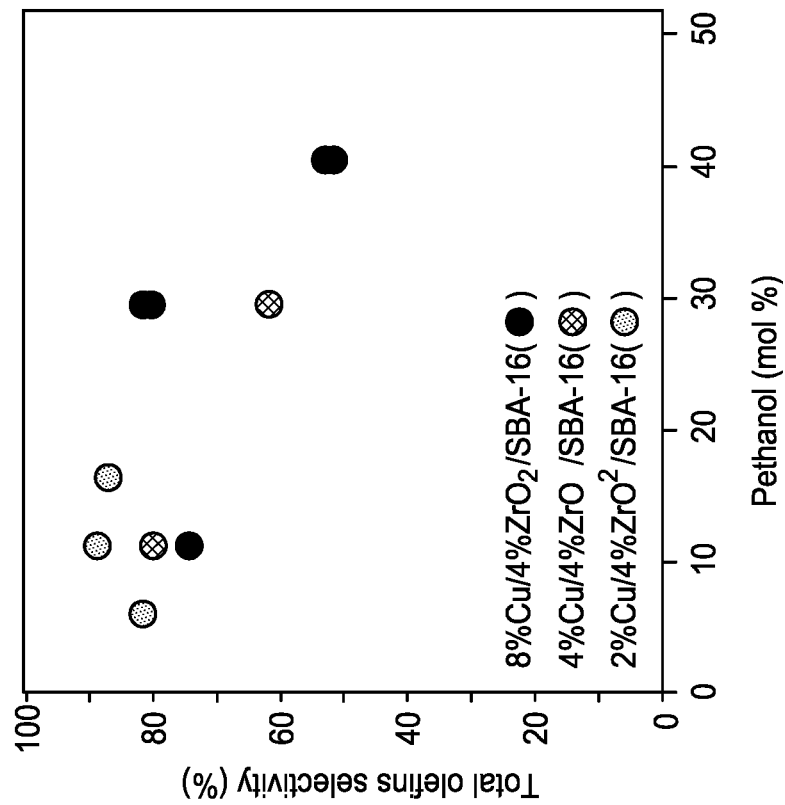

FIG. 3 is a graphical depiction of butene selectivity achieved utilizing embodiments of the disclosure. Butene selectivity is depicted as a function of the partial pressure of ethanol (Pethanol) for Cu/4ZrO$_2$/SBA-16 (SiO$_2$) catalysts. T=400° C., total pressure=100 psig, WHSV=0.7-1.8 hr$^{-1}$. Operating at Pethanol equal to 20-30 mol % can achieve higher linear butenes formation.

Figure 4:
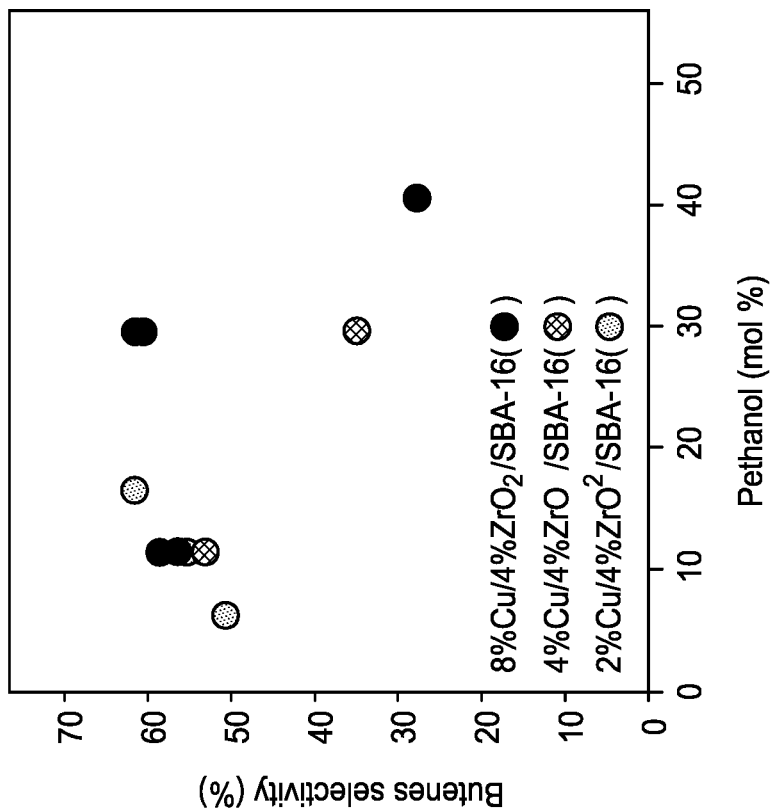

FIG. 4 is a depiction of total olefin selectivity utilizing embodiments of the disclosure. Total olefin selectivity is depicted as a function of the partial pressure of ethanol (Pethanol) for Cu/4ZrO$_2$/SBA-16 (SiO$_2$) catalysts. T=400° C., total pressure=100 psig, WHSV=0.7-1.8 hr$^{-1}$. The total olefins selectivity can be higher for Pethanol s 40 mol %.

Figure 5:
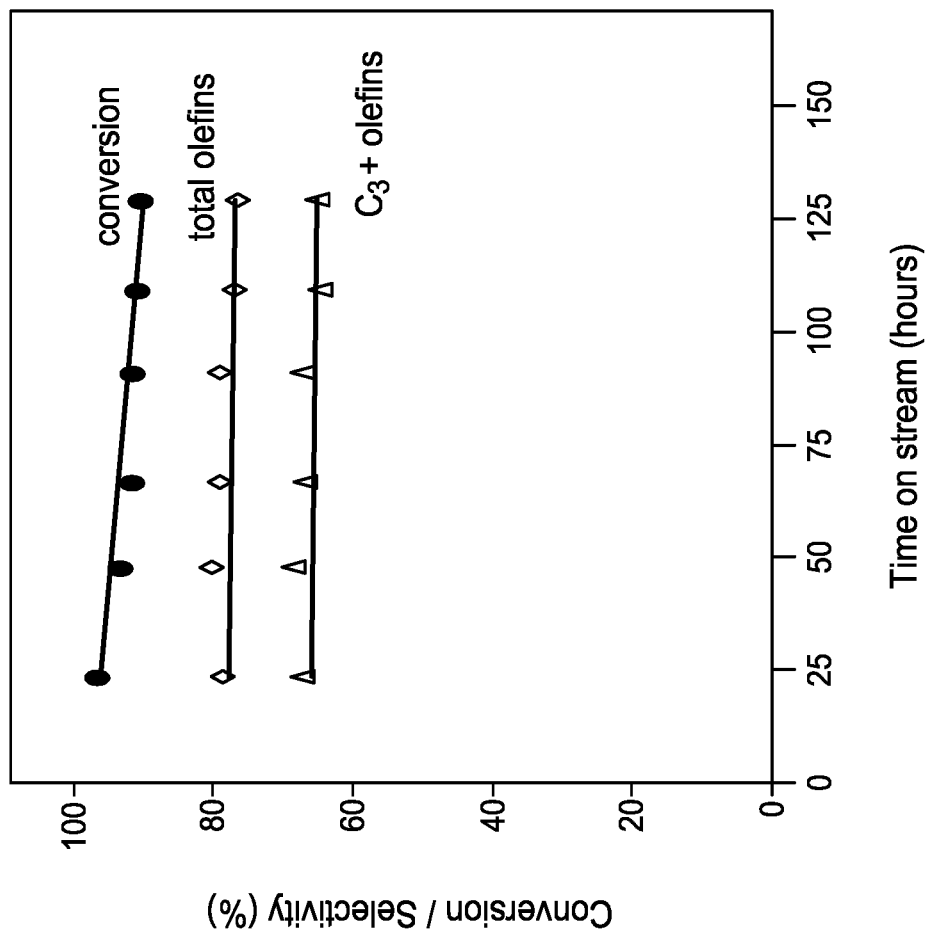

FIG. 5 is a depiction of catalytic performance utilizing embodiments of the disclosure. Evolution of the catalytic performance of 4% Cu/4% ZrO$_2$/SBA-16 (SiO$_2$) with time on stream for direct ethanol conversion into butenes-rich olefins is depicted. T=400° C., Pethanol=11% (molar), P=100 psig, WHSV=1.8 hr$^{-1}$. Only a relatively small decrease in conversion from 96% (TOS=24 hours) to 90% (TOS=139 hours) is observed. Both selectivities to total olefins and $C_{3+}$ olefins remain stable during the 129 hours on stream.

DESCRIPTION

This disclosure is submitted in furtherance of the constitutional purposes of the U.S. Patent Laws "to promote the progress of science and useful arts" (Article 1, Section 8).

Generally, butene is a valuable chemical commodity. Butenes may be found in industrial applications in the production of butadiene and solvents such as butanone. Butenes may also be used in the production of Hydrocarbons fuels such as for example gasoline, jet fuel or diesel. Previous processes converted ethanol to butenes via a two-step process that included first dehydrating ethanol into ethylene and then converting the ethylene into butenes.

Figure 1:
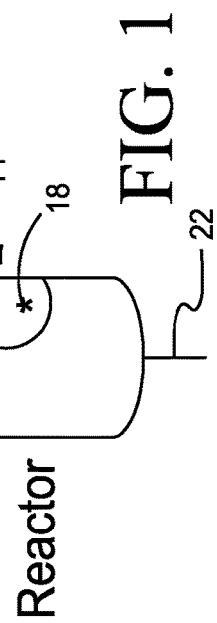
FIG. 1 is a depiction of a system according to an embodiment of the disclosure.

The present disclosure will be described with reference to FIGS. 1-5. Referring first to FIG. 1, a system 10 is shown that includes a reactor 12 that houses a catalyst 14 that includes a metal component 18 and an acidic support material 16. System 10 can also include a reactor inlet 20 and a reactor outlet 22. In accordance with example implementations, the reactor inlet can be coupled to both reactor 12 and at least one reactor reservoir not shown in this depiction, but shown in FIG. 2, for example, a feed from a pump (e.g., syringe or HPLC) that includes organic starting materials.

These starting materials can include ethanol and/or an aldehyde, wherein the aldehyde can include one or more of acetaldehyde, butyraldehydes, and/or crotonaldehyde. The starting materials can be aldehyde alone, for example, or a mixture of aldehyde and ethanol. In example implementations, with specific catalyst systems, the starting material can be solely ethanol. Of course, the starting materials may be mixed with materials that do not impact the reaction of the starting materials, water, for example. In these, example implementations, the starting materials can consist essentially of aldehydes and/or ethanol.

In accordance with other example implementations, other reservoirs can include hydrogen, or H$_2$, and this hydrogen can be provided to the reactor in equivalent or less than equivalent amounts to the ethanol and/or aldehyde starting materials. For example, $H_2$ is not necessary to form the butene-rich olefin products of the present disclosure.

Figure 2:
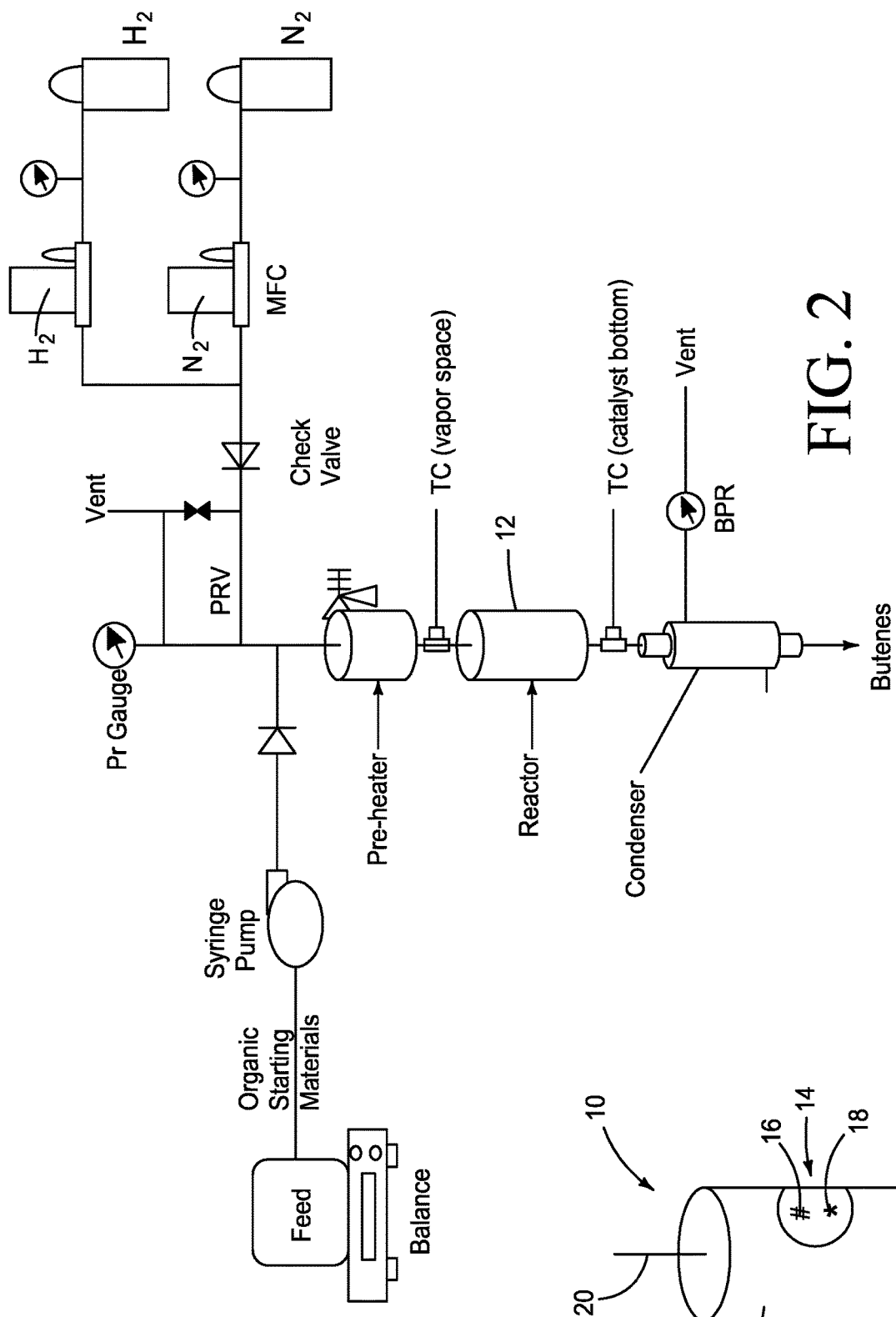
FIG. 2 is a depiction of an alternative system according to an embodiment of the disclosure.

In accordance with example implementations and with reference to FIG. 2 as shown, the $H_2$ can be supplemented with nitrogen, to provide a mixture of $H_2$ and $N_2$. In accordance with some example implementations, these materials can be operationally fed utilizing a computer processing system that is depicted as a computer on FIG. 2, to a pre-heater where the materials are preheated to the vapor phase, and then provided to a reactor 12, to be exposed to the metal and/or acidic support materials of the catalyst.

In accordance with some example implementations, the metals can include one or more of yttrium, copper, chromium, zinc, silver, zirconium, titanium, gallium, aluminum, and/or silica, in oxidized or elemental form. Where the starting material includes the aldehydes, these metals can be used. For example, when the starting materials include the mixture of ethanol and aldehydes, these same metals may be used. In some implementations, the starting materials can include ethanol. In these implementations, the metals can include one or more of yttrium, chromium, zinc, titanium, and/or gallium. The acidic support materials of the systems can include zeolites, carbon, aluminum, zirconium, and/or silica, for example, in elemental or oxidized form. In accordance with some example implementations, the reactor can be heated to between 200 and 450° C. In example configurations, the catalyst can include copper, and in those configurations, the copper amount of the catalyst can be between 0.5% and 20% (wt/wt %); or 1 and 16 (wt/wt %), and in other implementations, the catalyst can include a metal oxide such as zirconium, titanium, and/or zeolites. In some of these implementations these metals can be provided as oxides (e.g., $ZrO_2$, $TiO_2$, Zeolite) to provide acidity to the support materials such as Si (eg., $SiO_2$). In some of these implementations the metal oxide, such as the zirconium oxide, can be between 1 and 8 (wt/wt %) of the catalyst.

In accordance with example implementations, a butene-rich product can be achieved. This butene-rich product can include molar majorities of 1-butene and/or 2-butene, for example, in combination with other olefin materials such as butadiene.

In some example configurations, the reactant is ethanol, and the ethanol is exposed to a catalyst that can include one or more of Cu, Zr, and/or Si. In an embodiment, the systems and/or methods of the present disclosure can utilize aqueous ethanol feedstock. The separation of ethanol from water may not be necessary, which can eliminate an operation unit.

In other implementations, the reaction can include exposing an aldehyde to the catalyst. The catalyst in these implementations can include one or more of Cu, Zr, Si, Al, zeolite, Zn, and/or alumina. In example implementations, the catalyst being exposed to the aldehyde can include from 1-16 (wt/wt %) Cu and/or 1-8 (wt/wt %) $ZrO_2$. In other implementations, the catalyst can comprise Cu, $ZrO_2$, and $SiO_2$, and in other implementations, the catalyst can be supplemented with Zn and/or Ga. These aldehydes that are exposed to these catalysts can include as mentioned above acetaldehyde, butyraldehydes, and/or crotonaldehyde.

In accordance with at least some embodiments of the disclosure, a single step conversion of (aqueous) ethanol and/or aldehyde (e.g., acetaldehyde, butyraldehyde, crotonaldehyde) into butene-rich olefin product mixtures is provided. Example product mixtures resulting from the ethanol and/or aldehyde(s) conversion can contain primarily butenes and ethylene olefins mixed with $H_2$.

The butene-rich olefin product mixture can be selectively oligomerized into gasoline, jet, and/or diesel fuels. As such, oligomerization of mixed 1- and 2-butene produced by the processes described herein to jet fuel range hydrocarbon may be performed in the presence and absence of $H_2$ and/or ethylene.

As an example, 1-Butene is a chemical that can be converted into polybutene, making its main application as a comonomer in the production of certain kinds of polyethylene, such as linear low-density polyethylene (LLDPE). Additionally, or alternatively, 1-Butene has also been used as a precursor to polypropylene resins, butylene oxide, and butanone. Mixtures of 1-butene and 2-butene, as produced by the systems and methods described herein, can be oligomerized and hydrogenated into gasoline, jet fuel, diesel fuel, and/or into valuable fuel additives and lubricants.

The catalyst of the systems and/or methods of the present disclosure can include polyfunctional catalysts comprising a metal component with relatively weak hydrogenation ability (e.g., Cu) with mildly acidic support materials (e.g., $ZrO_2$ supported on $SiO_2$). These catalysts are active and selective for converting ethanol and/or aldehydes to 1- and 2-butenes in one single reactor under mild reducing conditions, for example (e.g., under $H_2$, T=400° C., P=7 bar).

Furthermore, catalyst formulation (i.e., effect of the nature of the support, promoters, addition, Cu loading and $ZrO_2$ loading) and process parameters such as $H_2$ concentration, ethanol partial pressure, and space velocity can impact conversion, selectivity, and stability (as shown in FIGS. 3-5 and the below tables), for example, the catalytic stability better for the Cu-based catalyst as compared to the Ag-based catalyst. The Cu-based catalyst presents higher resistance to coking and oxidation, which appears to provide superior durability.

TABLE 1

Catalytic performance of 4% Cu/4% $ZrO_2$/SBA-16 ($SiO_2$) for making linear butenes-rich olefins from ethanol, aldehydes or mixture of both.

| | Feed | | | | |
|---|---|---|---|---|---|
| | ethanol | acetaldehyde | Ethanol + acetaldehyde (2:1 mass) | ethanol + crotonaldehyde (2.3:1 mass) | butyraldehyde |
| Reaction Temperature (° C.) | 400 | 400 | 400 | 400 | 270 |
| Conversion (%) | 92.9 | 76.6 | 90.0 (acetaldehyde) 86 (ethanol) | 100.0 (crotonaldehyde) 80.8 (ethanol) | 98.9 |
| | | | Carbon based selectivity (%) | | |
| ethylene | 12.0 | 0.7 | 4.7 | 2.3 | 0.0 |
| propene | 2.9 | 1.4 | 2.7 | 2.9 | 0.0 |

TABLE 1-continued

Catalytic performance of 4% Cu/4% ZrO$_2$/SBA-16 (SiO$_2$) for making linear butenes-rich olefins from ethanol, aldehydes or mixture of both.

| | Feed | | | | |
|---|---|---|---|---|---|
| | ethanol | acetaldehyde | Ethanol + acetaldehyde (2:1 mass) | ethanol + crotonaldehyde (2.3:1 mass) | butyraldehyde |
| butenes | 54.0 | 10.5 | 69.2 | 67.5 | 7.2 |
| Total Olefins (C$_2$-C$_8$) | 80.3 | 14.0 | 86.7 | 77.6 | 7.2 |
| alkanes | 4.3 | 1.5 | 6.2 | 8.6 | 10.4 |
| butadiene | 0.0 | 0.0 | 0.0 | 0.0 | 0.0 |
| Di-ethyl-ether | 4.1 | 0.0 | 1.4 | 0.6 | 0.0 |
| acetaldehyde | 7.1 | 0.0 | 0.0 | 2.1 | 0.0 |
| butyraldehyde | 0.0 | 30.7 | 0.4 | 0.7 | 0.0 |
| 1-butanol | 0.2 | 8.4 | 1.0 | 2.3 | 82.4 |
| Other oxygenates* | 4.0 | 45.4 (mainly ethanol) | 4.3 | 8.1 | 0.0 |

TOS = 30-48 hours,
WHSV = 1.8-1.9 hr$^{-1}$,
P = 100 psig,
Pfeed = 10-12 mol %
*mainly: acetone, methanol, propanol, crotonaldehyde, crotyl alcohol, acetic acid, butanoic acid, ethyl acetate, methyl ethyl ketone, C$_5$$^+$ ketones, CO$_2$.

In accordance with Table 1, ethanol, aldehydes (i.e. acetaldehyde, butyraldehyde, crotonaldehyde) and mixture of them can all be converted to linear butenes-rich olefins in one single step over the Cu/ZrO$_2$/SBA-16 catalyst. Using acetaldehyde alone as a feedstock can provide relatively low butenes selectivity as compared to when ethanol and acetaldehyde are fed together. Ethanol can be a source of H for the hydrogenation of butyraldehyde.

Using butyraldehyde as a feedstock can provide a high ratio of 1-butanol/linear butenes. The hydrogenation of 1-butanol to linear butenes can occur at lower reaction temperatures. Higher reaction temperature can increase the conversion of 1-butanol to linear butenes.

TABLE 2

Impact of the space velocity (WHSV) on the catalytic performance of 4% Cu/4% ZrO$_2$/SBA-16 (SiO$_2$) for making linear butenes-rich olefins from ethanol.

| WHSVethanol (hr$^{-1}$) | 1.8 | 3.6 | 18.2 | 36.4 | 53.0 |
|---|---|---|---|---|---|
| Conversion (%) | 92.9 | 90.4 | 73.2 | 64.7 | 56.4 |
| Carbon based selectivity (%) | | | | | |
| ethylene | 12.0 | 10.5 | 6.1 | 4.8 | 5.8 |
| propene | 2.9 | 2.7 | 1.2 | 1.0 | 0.9 |
| butenes | 54.0 | 54.8 | 23.6 | 11.8 | 20.2 |
| Total Olefins (C$_2$-C$_8$) | 80.3 | 78.1 | 31.5 | 18.3 | 26.9 |
| alkanes | 4.3 | 3.8 | 10 | 9.5 | 0.8 |
| butadiene | 0.0 | 0.0 | 0.0 | 0.0 | 0.0 |
| Di-ethyl-ether | 4.1 | 3.0 | 3.1 | 2.4 | 2.7 |
| acetaldehyde | 7.1 | 9.7 | 29.9 | 36.8 | 44.1 |
| butyraldehyde | 0.0 | 0.4 | 4.5 | 7.2 | 6.1 |
| 1-butanol | 0.2 | 0.5 | 5.9 | 6.8 | 7.1 |
| Other oxygenates* | 4.0 | 4.5 | 15.1 | 19.0 | 12.3 |

T = 400° C.,
ethanol fed/gram catalyst = 1.9-2.2,
P = 100 psig,
Pethanol = 11 mol %
*mainly: acetone, methanol, propanol, crotonaldehyde, crotyl alcohol, acetic acid, butanoic acid, ethyl acetate, methyl ethyl ketone, C$_5$$^+$ ketones, CO$_2$.

As shown in Table 2, the conversion decreases from 92.9 to 56.4% as the Weight Hour Space Velocity (WHSV) increases from 1.8 to 53 hr$^{-1}$.

As the conversion increases, the selectivities to acetaldehyde, butyraldehyde and 1-butanol decrease while the selectivity to linear butenes increases indicating that acetaldehyde, butyraldehyde and 1-butanol can be intermediates products involved in the formation of butenes.

The highest total olefins selectivity of 80.3% (including 54% linear butenes) was obtained at 92.9% conversion.

TABLE 3

Effect of the H$_2$/N$_2$ ratio on the catalytic performance of 2% Cu/4% ZrO$_2$/SBA-16 (SiO$_2$) for making linear butenes-rich olefins from ethanol.

| H$_2$/N$_2$ ratio molar | 1/0 | 1/1 |
|---|---|---|
| Conversion (%) | 95.8 | 88.4 |
| Carbon selectivity (%) | | |
| ethylene | 26.9 | 37.6 |
| propene | 5.0 | 3.1 |
| butenes | 56.1 | 29.4 |
| Total Olefins (C$_2$-C$_8$) | 88.4 | 70.1 |
| alkanes | 3.3 | 2.5 |
| butadiene | 0.8 | 10.3 |
| Di-ethyl-ether | 2.2 | 9.6 |
| acetaldehyde | 1.7 | 5.2 |
| butyraldehyde | 0.0 | 0.0 |
| 1-butanol | 0.0 | 0.0 |
| Other oxygenates* | 3.9 | 2.3 |

T = 400° C.,
WHSV = 0.7 hr$^{-1}$,
TOS = 68-71 hours,
P = 100 psig,
Pethanol = 11 mol %
*mainly: acetone, methanol, propanol, crotonaldehyde, crotyl alcohol, acetic acid, butanoic acid, ethyl acetate, methyl ethyl ketone, C$_5$$^+$ ketones, CO$_2$.

As shown in Table 3, example product mixtures resulting from the ethanol and/or aldehyde(s) conversion can contain primarily butenes and ethylene olefins mixed with H$_2$. These butene-rich olefins can be oligomerized into gasoline, jet, and diesel range hydrocarbons. Operating under pure H$_2$ as opposed to a mixture of H$_2$/N$_2$ (50/50 molar) is preferred. It allows for improved hydrogenation activity leading to higher butadiene hydrogenation to linear butenes. Ethanol dehydrogenation to acetaldehyde is favored and ethanol dehydration is reduced in the presence of pure $H_2$ as compared to when operating with a mixture of $H_2+N_2$. Indeed, Di-ethyl-ether and ethylene dehydration products are higher when operating under a mixture of $H_2+N_2$.

TABLE 4

Impact of the nature of the catalyst support for the conversion of ethanol + acetaldehyde (2:1 mass) mixture to butenes-rich olefins.

| | Catalyst | | |
|---|---|---|---|
| | 4% Cu/4% $ZrO_2$/ SBA-16 ($SiO_2$) | 4% Cu/4% $ZrO_2$/ Dealuminated zeolite | 4% Cu/4% $ZrO_2$/ Aluminum silicate |
| Reaction Temperature (° C.) | 400 | 400 | 400 |
| Conversion (%) | 90.0 (acetaldehyde) | 20.3 (acetaldehyde) | 76.1 (acetaldehyde) |
| | 86 (ethanol) | 60.8 (ethanol) | 70.4 (ethanol) |
| Carbon based selectivity (%) | | | |
| ethylene | 4.7 | 7.2 | 0.4 |
| propene | 2.7 | 3.4 | 4.0 |
| butenes | 69.2 | 50.3 | 63.1 |
| Total Olefins ($C_2$-$C_8$) | 86.7 | 61.3 | 67.5 |
| alkanes | 6.2 | 4.8 | 9.6 |
| butadiene | 0.0 | 20.8 | 0.0 |
| Di-ethyl-ether | 1.4 | 1.7 | 13.3 |
| butyraldehyde | 0.4 | 1.9 | 0.0 |
| 1-butanol | 1.0 | 3.4 | 0.9 |
| Other oxygenates* | 4.3 | 6.1 | 8.7 |

TOS = 30-48 hours,
WHSV = 1.8 $hr^{-1}$,
P = 100 psig,
P ethanol = 11 mol %
*mainly: acetone, methanol, propanol, crotonaldehyde, crotyl alcohol, acetic acid, butanoic acid, ethyl acetate, methyl ethyl ketone, $C_5^+$ ketones, $CO_2$.

Direct conversion of ethanol+acetaldehyde mixture into butenes-rich olefins was demonstrated over $Cu/ZrO_2$ catalysts supported on SBA-16 ($SiO_2$), Dealuminated zeolite, and aluminum silicate catalysts. Si/Al ratio is ≥200 for the dealuminated zeolite.

TABLE 5

Effect of Cu loading on the catalytic performance of Cu/4$ZrO_2$/SBA-16 catalyst for direct conversion of ethanol to butenes-rich olefins.

| Cu loading (wt. %) | 2 | 4 | 8 | 16 | 1 | 2 | 4 |
|---|---|---|---|---|---|---|---|
| WHSVethanol ($hr^{-1}$) | 1.9 | 1.9 | 1.9 | 1.9 | 0.7 | 0.7 | 0.9 |
| Conversion (%) | 86.1 | 92.9 | 96.1 | 90.1 | 95 | 95.8 | 95.1 |
| Carbon based selectivity (%) | | | | | | | |
| ethylene | 28.2 | 12 | 15.8 | 8.3 | 9.6 | 26.9 | 14.9 |
| propene | 3.6 | 2.9 | 3.0 | 2.8 | 5.0 | 5.0 | 4.4 |
| butenes | 45.9 | 54 | 59.2 | 53.6 | 53.9 | 56.1 | 55.4 |
| Total Olefins ($C_2$-$C_8$) | 77.7 | 80.3 | 79.5 | 71.4 | 78.7 | 89.2 | 78.3 |
| alkanes | 1.8 | 4.3 | 8.5 | 17.3 | 1.9 | 3.3 | 8.5 |
| butadiene | 6.1 | 0.0 | 0.0 | 0.0 | 5.0 | 1.5 | 0.0 |
| Di-ethyl-ether | 6.7 | 4.1 | 2.4 | 2.0 | 2.2 | 2.2 | 2.9 |
| acetaldehyde | 5.5 | 7.1 | 5.2 | 5.5 | 3.4 | 1.7 | 5.8 |
| butyraldehyde | 0.0 | 0.0 | 0.5 | 0.3 | 0.7 | 0.0 | 0.1 |
| 1-butanol | 0.1 | 0.2 | 0.5 | 0.0 | 0.0 | 0.0 | 0.1 |
| Other oxygenates* | 2.1 | 4.0 | 3.4 | 3.5 | 7.6 | 2.1 | 4.3 |

T = 400° C.,
TOS = 48 hours,
P = 100 psig,
Pethanol = 11 mol %
*mainly: acetone, methanol, propanol, crotonaldehyde, crotyl alcohol, acetic acid, butanoic acid, ethyl acetate, methyl ethyl ketone, $C_5^+$ ketones, $CO_2$.

The effect of the Cu loading was determined for Cu/4ZrO2/SBA-16 ($SiO_2$) catalysts with 1 to 16 wt. % Cu. At similar WHSV, the conversion can increase from 86.1 to 96.1% while the Cu loading can increase from 2 to 8 wt. %. At higher Cu loading (i.e. >8%), the conversion can decrease due to increased Cu particle size. At similar conversion (90-97%), higher butenes selectivity of 59.2% can be achieved with the catalyst containing 8 wt %. Cu and highest total olefins selectivity of 89.2% can be obtained with the 2 wt. % Cu. The alkanes selectivity can increase with the Cu loading from 1 to 16 wt. % Cu due to increased hydrogenation activity provided by Cu.

TABLE 6

Effect of $ZrO_2$ loading on the catalytic performance of 8% Cu/$ZrO_2$/SBA-16 catalyst for direct conversion of ethanol to butenes-rich olefins.

| $ZrO_2$ loading (wt. %) | 4 | 4 | 6 | 6 |
|---|---|---|---|---|
| TOS (hours) | 24 | 49 | 23 | 42 |
| Conversion (%) | 92.5 | 88.2 | 94.9 | 91.0 |
| ethylene | 13.0 | 13.6 | 3.5 | 3.5 |
| propene | 4.5 | 4.1 | 2.1 | 1.8 |
| butenes | 62.4 | 61.4 | 28.8 | 27.6 |
| Total Olefins ($C_2$-$C_8$) | 81.8 | 81.0 | 84.4 | 64.6 |
| alkanes | 5.5 | 2.3 | 2.0 | 1.4 |
| butadiene | 0.0 | 0.0 | 0.0 | 0.0 |
| Di-ethyl-ether | 2.2 | 3.4 | 1.1 | 4.4 |
| acetaldehyde | 4.1 | 7.5 | 5.7 | 8.9 |
| butyraldehyde | 0.2 | 0.3 | 1.0 | 1.4 |
| 1-butanol | 0.5 | 0.8 | 0.4 | 0.5 |
| Other oxygenates* | 5.7 | 4.7 | 5.4 | 18.8 |

T = 400° C.,
WHSV = 1.8 $hr^{-1}$,
P = 100 psig,
Pethanol = 29 mol %
*mainly: acetone, methanol, propanol, crotonaldehyde, crotyl alcohol, acetic acid, butanoic acid, ethyl acetate, methyl ethyl ketone, $C_5^+$ ketones, $CO_2$.

The effect of the $ZrO_2$ loading was determined for 8% Cu/ZrO2/SBA-16 ($SiO_2$) catalysts with 4 wt. % and 6 wt. % $ZrO_2$. While highest linear butenes selectivity of 81.8% is obtained with the 8%/4% $ZrO_2$/SBA-16 ($SiO_2$) catalyst, the total olefins selectivity is the highest (i.e. 84.4%) with the 8%/6% $ZrO_2$/SBA-16 ($SiO_2$) catalyst due to the formation of $C_{4+}$ olefins.

TABLE 7

Effect of the promoter (i.e. Zn, Ga) on the catalytic performance of 1% Cu/4% $ZrO_2$/SBA-16 catalyst for direct conversion of ethanol to butenes-rich olefins.

| Promoter | none | none | 1 wt. % Zn | 1 w.t % Ga |
|---|---|---|---|---|
| TOS (hours) | 4 | 48 | 4 | 5 |
| Conversion (%) | 97.6 | 95.0 | 98 | 98.8 |
| Carbon based selectivity (%) | | | | |
| ethylene | 1.3 | 9.6 | 5.3 | 5.0 |
| propene | 2.0 | 5.0 | 5.4 | 3.2 |
| butenes | 35.7 | 58.9 | 73.9 | 46.4 |
| Total Olefins ($C_2$-$C_8$) | 43.3 | 78.7 | 90.4 | 65.6 |
| alkanes | 47.6 | 1.9 | 1.7 | 30.1 |
| butadiene | 0.0 | 5.0 | 0.0 | 0.0 |
| Di-ethyl-ether | 1.4 | 2.7 | 2.9 | 1.0 |
| acetaldehyde | 0.1 | 3.4 | 1.5 | 0.5 |

TABLE 7-continued

Effect of the promoter (i.e. Zn, Ga) on the catalytic performance of 1% Cu/4% ZrO$_2$/SBA-16 catalyst for direct conversion of ethanol to butenes-rich olefins.

| Promoter | none | none | 1 wt. % Zn | 1 w.t % Ga |
|---|---|---|---|---|
| butyraldehyde | 0.1 | 0.7 | 0.2 | 0.0 |
| 1-butanol | 0.0 | 0.0 | 0.0 | 0.0 |
| Other oxygenates* | 7.5 | 7.6 | 3.3 | 2.8 |

T = 400° C., TOS = 4-5 hours, WHSV = 0.7 hr$^{-1}$, P = 100 psig, Pethanol = 11 mol %.
*mainly: acetone, methanol, propanol, crotonaldehyde, crotyl alcohol, acetic acid, butanoic acid, ethyl acetate, methyl ethyl ketone, C$_5$$^+$ ketones, CO$_2$.

Zn promoter can enhance both linear butenes selectivity and total olefins selectivity of the 1% Cu/4% ZrO$_2$/SBA-16 (SiO$_2$) catalyst. Higher total olefins selectivity of 90.4% including 73.9% linear butenes selectivity can be obtained for 1% Cu/4% ZrO$_2$/SBA-16 (SiO$_2$) catalyst.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A method for preparing butenes, the method comprising exposing an aldehyde to a catalyst comprising Zn and/or Ga in addition to Cu, ZrO$_2$, and SiO$_2$ to form a butene-rich product that comprises 1-butene and/or 2-butene.

2. The method of claim 1 wherein the aldehyde is mixed with an ethanol and exposed to the catalyst to form the butene-rich product.

3. The method of claim 1 wherein the catalyst further comprises Al, zeolite, Zn, alumina, or a combination thereof.

4. The method of claim 3 wherein the catalyst comprises 0.5-20 (wt/wt %) Cu.

5. The method of claim 3 wherein the catalyst comprises 1-8 (wt/wt %) ZrO$_2$.

6. The method of claim 1 wherein the aldehyde comprises acetaldehyde, butraldehyde, crotonaldehyde, or a combination thereof.

* * * * *